_United States Patent_ [19]

Flatland

[11] 4,213,243
[45] Jul. 22, 1980

[54] ROTARY CONNECTOR FOR A DENTAL HANDPIECE

[76] Inventor: Lloyd P. Flatland, 15 Quisisana Dr., Kentfield, Calif. 94904

[21] Appl. No.: 534

[22] Filed: Jan. 2, 1979

[51] Int. Cl.² ............................................. A61C 1/12
[52] U.S. Cl. ..................................... 433/126; 433/82
[58] Field of Search ...................... 32/26, 27; 285/131, 285/132, 137 R

[56] References Cited

U.S. PATENT DOCUMENTS

| | | | |
|---|---|---|---|
| 1,119,916 | 12/1914 | Willis | 285/132 |
| 3,173,207 | 3/1965 | Burzlaff | 32/27 |
| 3,252,719 | 5/1966 | Bordon | 285/137 R |

_Primary Examiner_—Robert Peshock
_Attorney, Agent, or Firm_—Lothrop & West

[57] ABSTRACT

A rotary connector is insertable between a standard dental supply hose and a standard dental handpiece to carry the customary air and water supplies while permitting unlimited relative rotation between the hose and the handpiece around the longitudinal axis of the hose, the connector and the handpiece.

8 Claims, 7 Drawing Figures

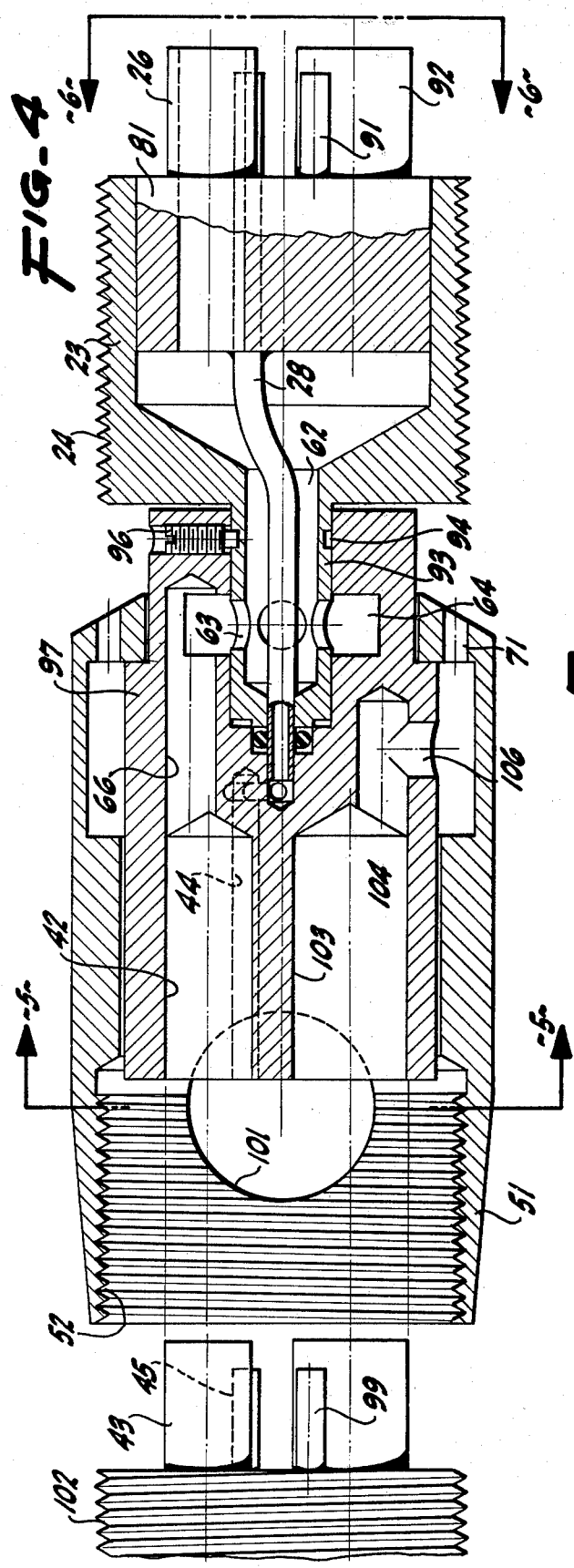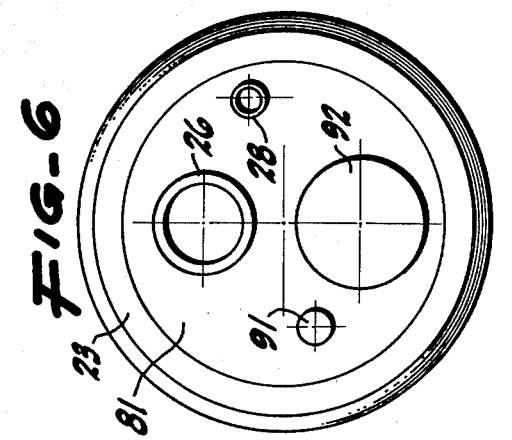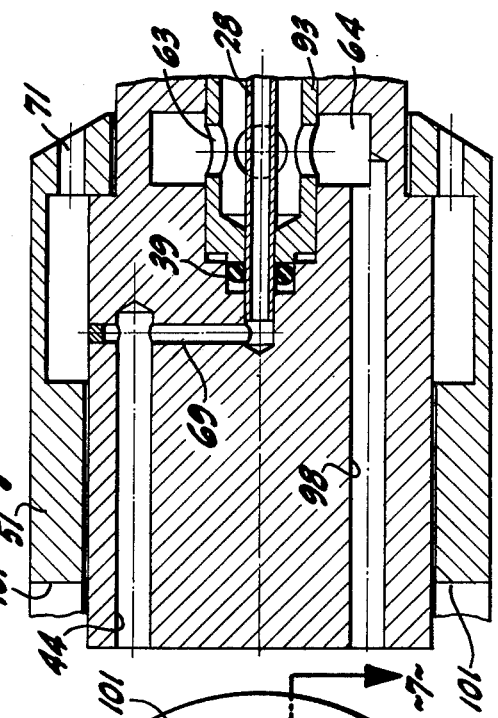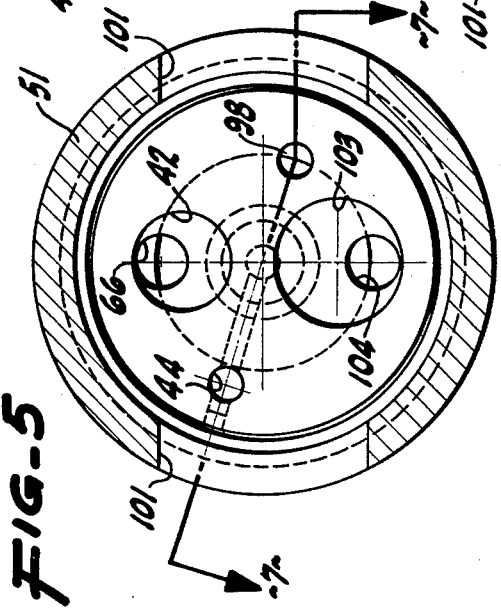

ROTARY CONNECTOR FOR A DENTAL HANDPIECE

BRIEF SUMMARY OF THE INVENTION

To obviate the ordinarily resulting muscular fatigue and strain normally ensuing upon the necessity of manipulating delicately a dental handpiece while the handpiece is rigidly connected to the sometimes relatively inflexible dental hose which supplies air and water to the handpiece, there is provided an insert between the standard handpiece and the standard dental hose. The insert affords a swivel interconnection along the longitudinal axis of the handpiece and which is effective to transfer air and water from the hose to the handpiece, thereby greatly reducing the strain and fatigue involved in operation.

BRIEF DESCRIPTION OF THE SEVERAL VIEWS OF THE DRAWINGS

FIG. 4 is an exploded view comparable to FIG. 2 but showing a modified form of rotary connector.

FIG. 5 is a cross-section through one end of the connector of FIG. 4, the plane of the view being indicated by the line 5—5 of FIG. 4.

FIG. 6 is a view of the other end of the connector shown in FIG. 4, the plane of the view being indicated by the line 6—6 of FIG. 4.

FIG. 7 is a detailed cross-section, the planes of which are indicated by the lines 7—7 of FIG. 5, showing a portion of the air and water mechanism of the device of FIG. 4.

DETAILED DESCRIPTION

Figure 1:
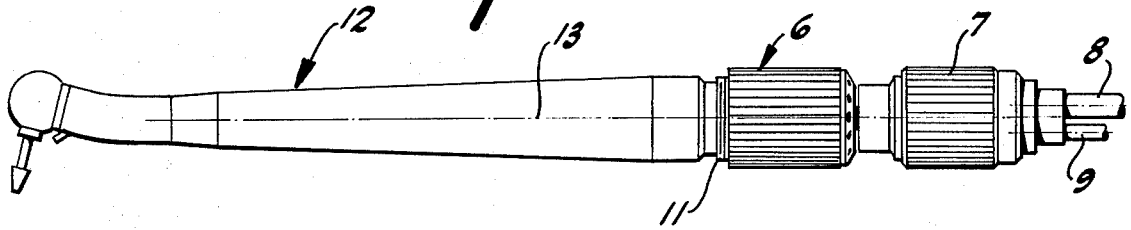
FIG. 1 is a side elevation of a dental handpiece and dental hose provided with one form of the rotary connector of the invention, certain portions of the hose being broken away.
Figure 2:
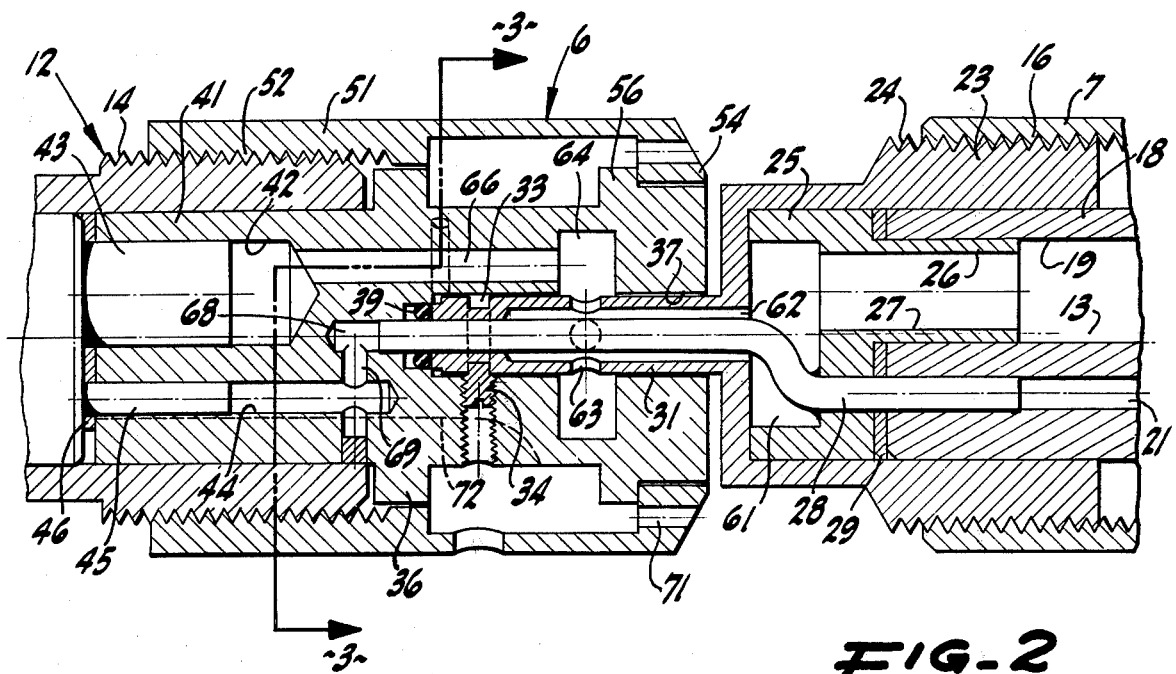
FIG. 2 is a cross-section to an enlarged scale and in an axial plane through a portion of the connector and associated handpiece and dental hose.

The connector, generally designated 6, shown in FIG. 1 is designed for ready attachment to one end of the customary dental hose fitting 7 connected to an air hose 8 and a water hose 9, all terminating in a standard connection in the customary way. The fitting 7 is normally received over one end 11 of a standard dental handpiece 12 of any of the usual constructions. The rotary connector 6 can be interposed between the standard fitting 7 and the standard handpiece 12 at will and can be detached therefrom as easily. The connector not only provides the customary fluid interconnections between the hose and the handpiece, but likewise without interfering with such connections also provides a rotary or swivel motion around the main axis 13 of the various elements. In use, the handpiece can easily be rotated and turned without interference or resistance by the sometimes rather stiff and relatively inflexible hose.

As it is ordinarily supplied, the handpiece 12 has an external thread 14 ordinarily interengaging with a mating internal thread 16 on the hose fitting 7. The fitting 7 incorporates relatively rigid body 18 inclusive of an internal air passage 19 from the hose 8 extending parallel to the axis 13 and also an internal water passage 21 from the hose 9 likewise extending parallel to the axis 13.

Forming part of the connector 6 is a plug 23 generally symmetrical about the axis 13 and having external plug threads 24 designed easily to interengage with the internal threads 16 and interfit the plug with the hose end fitting 7.

Preferably permanently seated within the generally hollow plug 23 is a flanged insert 25 having a relatively large air inlet passage tube 26 and projecting therefrom to fit snugly within the air passage 27 of the hose itself. Similarly, the insert 25 incorporates a tube 28 extending in an axial direction from the plug and designed easily to fit into the standard water passage 21 in the hose. A gasket 29 is interposed between the end face of the insert 25 and the end of the hose mechanism, so that when the fitting thread 16 is tightly engaged with the plug thread 24, the gasket is slightly compressed and there is no possibility of leakage between the hose end and the plug.

Also formed preferably integrally with the plug is a spindle 31 of a large diameter and extending along the central axis 13 to a substantial distance. The spindle is preferably hollow for a portion only of its length. The water tube 28, initially offset, is conformed to follow along the axis 13 and so to lie easily nested within the large spindle 31 and leaving an adequate air flow space of annular configuration therebetween.

In order that the parts may be appropriately held together, the spindle near one end has an annular groove 33 into which projects the end of a set screw 34 seated radially in a socket 36 generally symmetrical about the axis 13. The socket has a slightly enlarged internal bore 37 easily accommodating the spindle 31 for rotation. A sealing ring or O-ring 39 is interposed between the groove 33 and the end of the tube 28 so that there is no normal leakage therebetween.

The socket 36 at its remote end is provided with a smooth hub 41 designed to fit into the end of the handpiece 12. The hub 41 has a relatively large bore 42 fitting over a projecting air tube 43 on the handpiece and also has a relatively smaller water outlet passage 44 designed to receive the water tube 45 forming part of the customary handpiece. There is a gasket 46 between the meeting faces of the socket and the handpiece. Pressure is brought against the gasket by a collar 51 having internal threads 52 at one end designed to interengage with the external threads 14 of the handpiece. The collar 51 at the other end has an inturned flange 54 arranged to abut and rotate relative to a bead or shoulder 56 on the socket. The collar, when rotated, simply abuts against the shoulder and draws the parts together as tightly as desired to compress the flange and generally to make a firm assembly. Yet, the firm assembly does not interfere with relative rotation between the spindle 31 and the socket 36. Thus, there is easy relative rotation around the axis 13 between the hose and the handpiece.

The air inlet passage 26 is continued from the hose into a chamber 61 within the insert 25, from which flow continues through the annular space 62 between the interior of the spindle 31 and the exterior of the water tube 28. In the spindle are radial apertures 63 permitting air flow from the interior of the spindle through the apertures into an annular chamber 64 formed in the socket and having an outlet passage 66 opening at one end into the chamber 42. There is unhampered air flow from the hose through the entire fitting into the handpiece. While there can be some slight leakage of air between the outside of the spindle and the inside of the socket, this is normally very minor and is not detrimental, so that no particular sealing means are provided.

Water under pressure in the passage 21 flows easily into and travels throughout the length of the tube 28 within the spindle. The end of the tube 28 journalled within an axial passage 68 having a radial connector 69 to the passage 44 in the socket which communicates with the water tube 45. In this fashion, water from the hose is readily taken to the handpiece without any substantial leakage whatsoever due to the effectiveness of the O-ring 39. However, should the O-ring ultimately start to leak, then such leakage past the O-ring flows into the interior of the bore 37 and then flows through a radial duct 70 to discharge to the interior of the collar 51. The leakage blows out, with air being discharged, through a ring of axial passages 71 provided at intervals in the collar flange 54 and opening to the atmosphere. Any slight water leak thus carried away from the mechanism is immaterial since it is dispersed in the discharging air.

Figure 3:
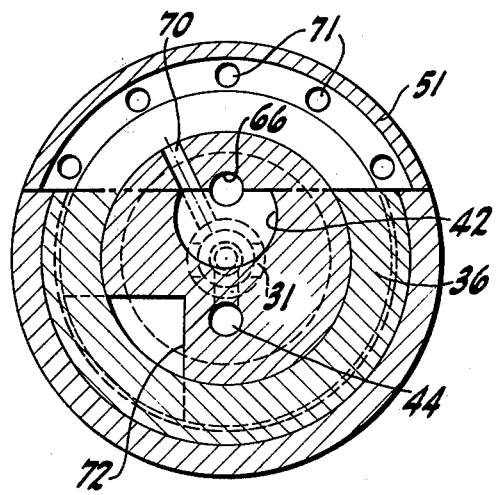
FIG. 3 is a cross-section, the planes of which are indicated by the lines 3—3 of FIG. 2.

Return air leaving the handpiece 12 through the customary channel finds its way into a cutaway groove 72 (FIG. 3) which opens on the outside of the socket and within the collar. Such discharged air joins air within the collar 51 and finally escapes through the various orifices 71 to the atmosphere.

With this connector, therefore, it is possible to afford in the usual dental hose and handpiece combination an axially rotatable swivel connection so that the strain on the dentist's hand and arm is reduced very substantially. It is possible to do so while not interfering at all with the normal supply and discharge of air and supply of water to the handpiece.

While the handpiece already described is of a generally standard nature in the field, there is another commercial form of handpiece and hose connection which is similar but has additional fittings or connections. As shown particularly in FIGS. 4 through 7, the construction in general is about the same as already described, and similar reference numerals apply to similar parts, but the hose utilized with the FIG. 4 plug 81 is designed to connect to an air inlet passage 19 and a water inlet passage 21. The fitting is originally intended to have a separate air exhaust passage and a separate water passage, but in this instance those portions of the hose are not used actively, but are engageable with a dummy connector 91 for the water passage and a dummy connector 92 for the air passage. These are utilized in order to make a tight interconnection but otherwise do not function.

The interior of the plug 81 of FIG. 4 is generally like the mechanism previously described, except that the spindle 93 has a circumferential groove 94 near the plug rather than far from it, so that a set screw 96 in the socket 97, displaced from its position in FIG. 1, is readily accessible.

In addition to the passages as previously described for air and water, there is tapped off of the chamber 64 a chip air spray duct 98 which extends in an axial direction and is intended to be engaged by a chip air spray projection 99 forming part of the handpiece.

The somewhat different interior arrangement of the parts and the additional interconnections to be made are readily discerned through an inspection orifice 101 through the collar. An individual looking through the opening 101 can see the interengagement between the handpiece projections and the receptacles on the swivel or rotary connector.

In this instance, exhaust air from the handpiece in the customary fitting 102 travels directly into a passageway 103 with which it is socketed in the fitting, and such air then travels through connecting passageways 104 and 106 into the customray discharge openings 71 in the collar flange.

The two described connectors are substantially identical in their functions, but are slightly rearranged in order to accommodate the two principal kinds of handpieces and hose connectors currently in use.

In both instances there is readily provided or removed a rotary connector affording an unlimited amount of relative rotation between the hose and the handpiece about a longitudinal axis, thus greatly reducing the strain on the using dentist.

I claim:

1. A rotary connector for a dental handpiece having an external handpiece thread and for a dental hose having a mating internal hose thread comprising a plug generally symmetrical about an axis and having a plug external thread adapted to engage said internal hose thread, a spindle extending from said plug along said axis, a socket generally symmetrical about said axis and journalled on said spindle for rotation about said axis, means interengaging said socket and said spindle for releasably precluding axial displacement thereof, a shoulder on said socket, a collar having a flange adapted to abut said shoulder and having internal threads adapted to engage said external handpiece thread, means defining in said plug an air inlet passage open to said hose and extending partway through said spindle and open through an orifice in the side of said spindle, means defining in said socket an air outlet passage open to said orifice and open to said handpiece, means including a tube defining in said plug a water inlet passage open to said hose and extending through said air inlet passage and projecting axially from said spindle, and means defining in said socket a water outlet passage open to said tube and open to said handpiece.

2. A device as in claim 1 including a seal between said spindle and said socket for precluding water leakage therebetween.

3. A device as in claim 1 including means defining a duct in said socket for conducting water leakage from between said spindle and said socket to the exterior of said socket.

4. A device as in claim 1 including means for conducting exhaust air from said handpiece through said socket to the interior of said collar, and means for conducting exhaust air from the interior of said collar to the exterior of said collar.

5. A device as in claim 1 in which said means defining in said plug an air inlet passage open to said hose is in alignment in an axial direction with said means defining in said socket an outlet passage open to said handpiece.

6. A device as in claim 1 in which said means defining in said plug a water inlet passage open to said hose is in alignment in an axial direction with said means defining in said socket a water outlet passage open to said handpiece.

7. A device as in claim 1 including means defining in said plug a second air outlet passage open to said air outlet passage open in an axial direction to said handpiece.

8. A device as in claim 1 in which said collar extends axially substantially beyond the end of said plug, and means defining an aperture in said collar exposing said end of said plug to view.

* * * * *